United States Patent [19]

Farina et al.

[11] Patent Number: 4,632,982

[45] Date of Patent: Dec. 30, 1986

[54] TRIPHENYLMETHYL AZO AND HYDRAZINO SUBSTITUTED PYRIDAZINES

[75] Inventors: Carlo Farina, Valsolda; Giorgio Pifferi, Milan; Mario Pinza, Corsico, all of Italy

[73] Assignee: I.S.F. S.p.A., Milan, Italy

[21] Appl. No.: 831,434

[22] Filed: Feb. 20, 1986

Related U.S. Application Data

[62] Division of Ser. No. 600,407, Apr. 16, 1984, Pat. No. 4,575,552.

[30] Foreign Application Priority Data

Apr. 28, 1983 [IT] Italy ................................ 20813 A/83

[51] Int. Cl.$^4$ ................ C07C 107/04; C07D 237/12; C07D 237/20
[52] U.S. Cl. ........................................ 534/753; 544/224
[58] Field of Search ........................ 544/224; 534/753

[56] References Cited

U.S. PATENT DOCUMENTS

| 3,642,792 | 2/1972 | Bellasio et al. | 544/224 |
| 3,769,278 | 10/1973 | Pifferi | 544/224 |
| 4,002,753 | 1/1977 | Carpi et al. | 544/224 |
| 4,086,343 | 4/1978 | Dorigotti et al. | 544/224 |

*Primary Examiner*—Donald G. Daus
*Assistant Examiner*—Stephen M. Kapner
*Attorney, Agent, or Firm*—Wenderoth, Lind & Ponack

[57] ABSTRACT

Preparation of ethyl {6-[ethyl-(2-hydroxypropyl)amino]-3-pyridazinyl}hydrazino carboxylate is disclosed, from 3-chloro-6-hydrazinopyridazine in protected form, which is oxidized to yield the corresponding azo derivative, which is treated with ethyl-(2-hydroxypropyl)amine in the presence of strong bases, the corresponding amino derivative being subjected to reduction and deprotection, and finally acylated to yield ethyl{6-[ethyl-(2-hydroxypropyl)amino]-3-pyridazinyl}hydrazinocarboxylate.

4 Claims, No Drawings

TRIPHENYLMETHYL AZO AND HYDRAZINO SUBSTITUTED PYRIDAZINES

This is a divisional application of Ser. No. 600,407, filed on Apr. 16, 1984, now U.S. Pat. No. 4,575,552.

BACKGROUND OF THE INVENTION

Field of the Invention

This invention relates to a method of preparing a compound having a pyridazino structure, namely ethyl{6-[ethyl-(2-hydroxypropyl)amino]-3-pyridazinyl}hydrazinocarboxylate. This compound exhibits a strong and lasting antihypertensive activity and causes retention of neither sodium nor liquids in the patients treated with it.

SUMMARY OF THE INVENTION

The method according to this invention affords very high yields of ethyl{6-[ethyl-(2-hydroxypropyl)amino]-3-pyridazinyl}hydrazinocarboxylate through reactions which occur in extremely mild conditions, at room temperature and pressure.

In practice the starting material which comprises 3-chloro-6-hydrazinopyridazine is first protected at the hydrazino moiety, for example in the form of 3-chloro-6-(2-triphenylmethylhydrazino)pyridazine II, the reaction with the protecting halotriphenylmethane being carried out at 0°–80° C., preferably at room temperature in a suitable solvent like dichloromethane, or THF or chloroform. Then compound II is oxidized with an oxidizing agent selected from potassium permanganate, potassium dichromate or sodium hypochlorite in a suitable solvent like a halogenated hydrocarbon solvent such as dichloromethane or chloroform. Thus the reaction for example with potassium permanganate is carried out at a temperature of from 0° to 40° C., preferably at room temperature, by preferably operating in phase transfer, in the presence of catalytic amounts of a suitable catalyst such as a quaternary ammonium salt.

The corresponding azo derivative III thus formed is, in turn, treated with an aminoalcohol in the presence of a base such as potassium tert-butylate or sodium hydride which salifies the aminoalcohol reagent. This reaction with the aminoalcohol is carried out at 0°–50° C., preferably at room temperature in a suitable solvent.

The aminoderivative IV thus obtained is reduced to the compound of the formula V by hydrogenation with palladium on carbon, or with reducing agents such as sodium borohydride or sodium hydrosulphite at a temperature of from 0° to 50° C., preferably at room temperature in an alcohol or other suitable solvent.

Compound V is then deprotected by hydrolyses in the presence of mineral acids, in an alcoholic solvent, at 0°–100° C., preferably at room temperature, to yield the corresponding derivative VI, which is finally acylated with ethyl chlorocarbonate at a temperature of from −10° C. to +20° C., preferably 0° C. in a suitable solvent, such as water, an alcohol, acetone, or their mixtures to obtain the desired compound.

This method may be summarized as follows:

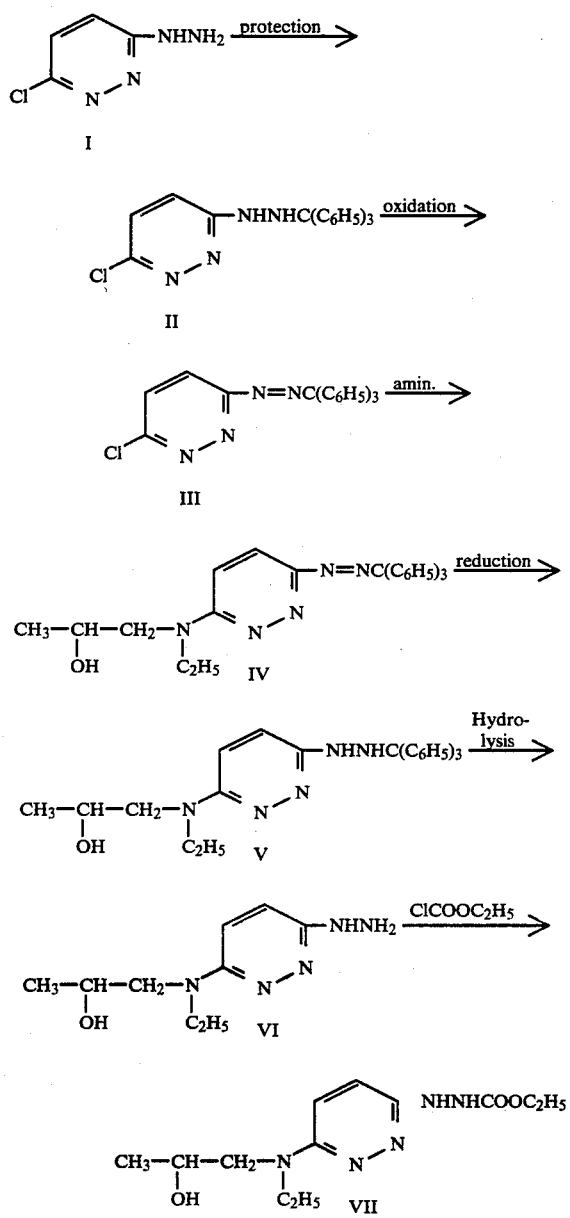

DETAILED DESCRIPTION OF THE PREFERRED EMBODIMENTS

The Example which follows purports to further illustrate the invention without limiting its scope.

EXAMPLE

Ethyl{6-[ethyl-(2-hydroxypropyl)amino]-3-pyridazinyl}hydrazinecarboxylate

To a suspension comprising 70 g 3-chloro-6-hydrazinopyridazine and 67 ml triethylamine in 1500 ml dichloromethane there is added drop by drop a solution of 135 g chlorotriphenylmethane in 500 ml dichloromethane. This is stirred at room temperature for one hour, washed with water, and then with a saturated ammonium sulphate solution. The organic phase is rendered anhydrous and the solvent removed by evaporation. The residue is triturated with petroleum ether, and 159 g of 3-chloro-6-(2-triphenylmethylhydrazino)-pyridazine melting at 163°–165° C. are obtained.

To a solution of 159 g of 3-chloro-6-(2-triphenylmethylhydrazino)pyridazine in 1500 ml dichloromethane, a solution of 47 g potassium permanganate in 600 ml water is added. 5 g of cetyltrimethylammonium bromide are added and the whole is stirred powerfully for one hour. The phases are separated, the organic phase is then washed in order with water, sodium bisulphite, and ammonium sulphate (saturated solution). This is rendered anhydrous and the solvent is removed by evaporation. The resulting yellow solid is triturated with petroleum ether to yield 144 g of 3-chloro-6-triphenylmethylazopyridazine melting at 125°–126° C.

To a 50% suspension of 1.5 g sodium hydride in 100 ml tetrahydrofuran, 3 g ethyl-(2-hydroxypropyl)amine are added; this is stirred at room temperature for 30 minutes, thereafter 4.5 g of 3-chloro-6-triphenylmethylazopyridazine are added. Stirring is maintained for 5 minutes, the organic phase is washed with a saturated solution of sodium chloride, rendered anhydrous and evaporated to dryness under a vacuum. The residue is taken up with ethyl alcohol, diluted with water, and the precipitate is collected under a vacuum which is then triturated with diisopropyl ether to yield 4 g of 3-[ethyl-(2-hydroxypropyl)amino]-6-triphenylmethylazopyridazine melting at 137° C. (with decomposition). A solution of 3 g of 3-[ethyl-(2-hydroxypropyl)amino]-6-triphenylmethylazopyridazine in 300 ml ethyl alcohol and 50 ml tetrahydrofuran containing 300 mg 5% palladium on carbon is hydrogenated at room temperature and pressure. The catalyst is filtered out, then the residue is evaporated and triturated with diethyl ether to yield 2.5 g of 3-[ethyl-(2-hydroxypropyl)amino]-6-(2-triphenylmethylhydrazino)pyridazine melting at 122° C. (with decomposition). A solution of 2 g of 3-[ethyl-(2-hydroxypropyl)amino]-6-(2-triphenylmethylhydrazino)pyridazine in 100 ml absolute ethyl alcohol is mixed with 2.5 ml concentrated hydrochloric acid and stirred for 15 minutes at room temperature. This is evaporated under a vacuum and the residue taken up with isopropyl alcohol. This is diluted with diisopropyl ether to yield 1.2 g of 3-[ethyl-(2-hydroxypropyl)amino]-6-hydrazinopyridazine dihydrochloride melting at 208°–212° C. (with decomposition).

To a solution comprising 1.4 g of 3-[ethyl-(2-hydroxypropyl)amino]-6-hydrazinopyridazine dihydrochloride in 20 ml water and 10 ml isopropyl alcohol there are carefully added under agitation and in a nitrogen atmosphere 1.7 g potassium bicarbonate. There is added dropwise into the reaction mixture, maintained at 0° C., within one hour, 5.9 g of ethyl chlorocarbonate, thereafter the reaction is allowed to proceed at room temperature for two hours, is maintained at 0° C. overnight, and the precipitate is collected under vacuum, and is then washed with cold water to yield 7 g of ethyl{6-[ethyl-(2-hydroxypropyl)amino]-3-pyridazinyl}hydrazinecarboxylate melting at 158°–162° C.

We claim:

1. A compound of the structure:

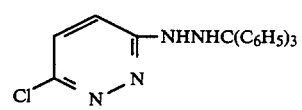

(II)

2. A compound of the structure:

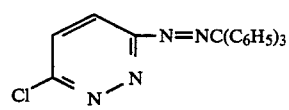

(III)

3. A compound of the structure:

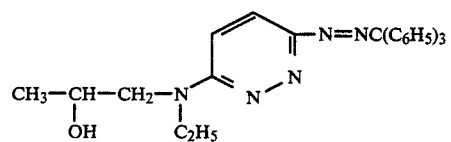

(IV)

4. A compound of the structure:

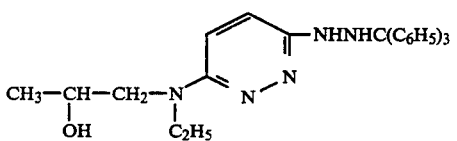

(V)

* * * * *